United States Patent
White et al.

(10) Patent No.: US 8,100,953 B2
(45) Date of Patent: Jan. 24, 2012

(54) BONE PLATE WITH COMPLEX, ADJACENT HOLES JOINED BY A RELIEF-SPACE

(75) Inventors: Patrick White, West Chester, PA (US); Steve Forbes, Exton, PA (US); Gary Thau, Morgantown, PA (US)

(73) Assignee: Swiss Pro Orthpedic SA, Bienne (CH)

( * ) Notice: Subject to any disclaimer, the term of this patent is extended or adjusted under 35 U.S.C. 154(b) by 391 days.

(21) Appl. No.: 12/399,170

(22) Filed: Mar. 6, 2009

(65) Prior Publication Data

US 2009/0171399 A1 Jul. 2, 2009

Related U.S. Application Data

(63) Continuation-in-part of application No. 12/307,451, filed as application No. PCT/IB2007/001895 on Jul. 6, 2007.

(60) Provisional application No. 60/806,728, filed on Jul. 7, 2006, provisional application No. 60/806,730, filed on Jul. 7, 2006.

(51) Int. Cl.
*A61B 17/80* (2006.01)
(52) U.S. Cl. .......... 606/280; 606/286
(58) Field of Classification Search .......... 606/280, 606/281, 286, 282, 71, 70
See application file for complete search history.

(56) References Cited

U.S. PATENT DOCUMENTS

| | | | |
|---|---|---|---|
| 3,659,595 A | 5/1972 | Haboush | |
| 3,716,050 A | 2/1973 | Johnston | |
| 4,611,581 A | 9/1986 | Steffee | |
| 4,696,290 A | 9/1987 | Steffee | |
| 5,057,111 A | 10/1991 | Park | |
| 5,209,751 A | 5/1993 | Farris et al. | |
| 5,261,910 A | 11/1993 | Warden et al. | |
| 5,324,290 A | 6/1994 | Zdeblick et al. | |
| 5,364,399 A | 11/1994 | Lowery et al. | |
| 5,681,311 A | 10/1997 | Foley et al. | |
| 5,709,686 A | 1/1998 | Talos et al. | |
| 6,406,478 B1 | 6/2002 | Kuo | |
| 6,623,486 B1 * | 9/2003 | Weaver et al. | 606/281 |
| 6,669,701 B2 | 12/2003 | Frigg | |
| 6,719,759 B2 | 4/2004 | Wagner et al. | |
| 7,354,441 B2 | 4/2008 | Frigg | |
| 2002/0183752 A1 * | 12/2002 | Steiner et al. | 606/69 |
| 2003/0040748 A1 * | 2/2003 | Aikins et al. | 606/70 |
| 2004/0181228 A1 | 9/2004 | Wagner et al. | |
| 2004/0260291 A1 * | 12/2004 | Jensen | 606/69 |

(Continued)

FOREIGN PATENT DOCUMENTS

EP 1468655 A2 10/2004

(Continued)

*Primary Examiner* — Thomas C. Barrett
*Assistant Examiner* — Melissa A Golob
(74) *Attorney, Agent, or Firm* — Michael E. Scalise (57) ABSTRACT

A bone plate is described which is adapted for use in situ to fix a spatial relationship of at least two bone parts. The bone plate has at least one pair of the bone screw apertures that are adjoined by a relief-space contiguous with the open space of the screw apertures themselves. An adjoined aperture pair forms a complex aperture and has a center-to-center distance d of the apertures along an axis running through the centers of the apertures. The center-to-center distance d is equal to or greater than the sum of the radii (r1+r2) of the heads of the individual bone screw used with the aperture pair.

23 Claims, 8 Drawing Sheets

U.S. PATENT DOCUMENTS

| | | |
|---|---|---|
| 2005/0015089 A1* | 1/2005 | Young et al. .................... 606/69 |
| 2005/0049594 A1* | 3/2005 | Wack et al. ..................... 606/69 |
| 2005/0096657 A1* | 5/2005 | Autericque et al. ............. 606/69 |
| 2005/0216027 A1* | 9/2005 | Suh et al. ....................... 606/104 |
| 2006/0264946 A1* | 11/2006 | Young ............................. 606/69 |
| 2010/0292696 A1* | 11/2010 | Chantelot et al. ............... 606/70 |

FOREIGN PATENT DOCUMENTS

| | | |
|---|---|---|
| EP | 1468655 | 5/2006 |
| WO | 01/54601 A1 | 8/2001 |
| WO | WO2004084701 * | 10/2004 |
| WO | 2006/014391 A1 | 2/2006 |

* cited by examiner

BONE PLATE WITH COMPLEX, ADJACENT HOLES JOINED BY A RELIEF-SPACE

CROSS-REFERENCE TO RELATED APPLICATIONS

The present application claims priority as continuation-in-part of U.S. patent application Ser. No. 12/307,451, filed on Jan. 5, 2009; which also claims priority as a 371 of international application PCT/IB2007/001895, filed on 6 Jul. 2007; which further claims the benefit of prior filed U.S. Provisional Patent Application Ser. Nos. 60/806,728 filed 7 Jul. 2006, and 60/806,730 also filed 7 Jul. 2006.

FIELD OF THE INVENTION

The present invention is in the field of surgically implanted orthopedic devices, implants and prostheses used in orthopedic surgery. More specifically, the present invention relates to bone plates used to reinforce fractured bones and thus to promote healing.

BACKGROUND OF THE INVENTION

A compressive screw system, also known as the DCS system, is a bone plate system that has been used in trauma surgery for many years. The procedures for use of this system are well documented by the AO Institute (Davos, Switzerland), an institute having as one of its goals, the promotion of new orthopedic surgical procedures. This system included a bone plate having slots communicating therethrough. A land in which the slot is wider at one end defines a stepped surface adjacent the portion of the slot that extends through the bone plate. The stepped surface is generally cut with a spherical endmill, thus creating a spherical stepped surface.

In a still further development, there exists bone plates which have individual threaded and non-threaded apertures interspersed along the length of the plate. In this and other designs, the distance between holes has become a standard. Although an improvement over the inserts noted above, the locking positions are pre-defined and only available in limited locations, which also reduce surgical flexibility. In another product variation, expandable, lockable inserts enter into the slots of a standard bone plate. When the bone screw passes through one of these inserts and is torqued down, the insert expands and locks the screw in place. However, this insert is locked in a secondary operation. This is not desirable because this requires more operating room time and adds complexity to the procedure. Further, the inserts must be added in the specific location before the plate is fixed to the bone and cannot be subsequently inserted. This limits the choice of placement during surgery if the need arises.

Also, the above insert designs rely on a friction lock via contact between two simple surfaces. Simple surface friction locks are not reliable and come loose more easily than threaded locked holes. The result of such a design is inferior to that of the threaded plate and screw designs discussed below.

In U.S. Pat. No. 5,002,544, there is shown an osteosynthetic pressure plate having a cross-section transverse to the longitudinal axis of the plate at least at one point being wider toward the upper surface than toward the lower surface and the plate having recesses in the lower surface so that upon application to a bone there is space between the bone and the plate. The cross-section between the screw holes is reduced, preferably to the extent that the resistance of the plate to bending in this area is less than in the area of the holes. Because of the reduced bend resistance between the holes, the plate can more easily be adapted to conform to the anatomy of the bone. Furthermore, this can be done without deformation of the holes, thus minimizing the resulting loss of fatigue strength and minimizing the misfit of the screw heads.

Further, U.S. Pat. No. 5,709,686 describes a bone plate that has recesses or reduced thickness portions on its sides, between threaded apertures. Although the purpose is not specifically described, these recesses appear to function to avoid warpage of the threaded portions when the bone plate is bent. However, when such a bone plate is fixed to a bone, these discontinuous recesses are exposed and may potentially come into contact with and potentially aggravate muscle tissue.

Still further, U.S. Pat. No. 5,733,287 shows, in FIG. 4, a plate that has transverse cuts 13 and a longitudinal cut 14 on the lower surface 7 to reduce contact between the plate and bone. Due to the transverse undercuts 13, the cross-section 15 between the holes is already significantly reduced and therefore is not further decreased by an additional groove 10 on the upper surface 6 as in the embodiment according to FIG. 3. To avoid a cross-section that is too thin, the groove 10 on the upper surface 6 is made discontinuous in short segmental grooves 16 providing a smooth transition into and out of the holes 8.

In yet another solution, PCT application no. WO01/54601 combines the features of the DCS system discussed above with a locking screw. Such a system is known as the combi-slot. In this design, the stepped surface of the slot is generally ramped or tapered so as to be deeper at one end than at another. This enables the positioning and selective fixing of the bone plate for compressing two bone fragments together with a preload created by wedging action. In this manner, the bones are placed in a position that the surgeon believes would best promote healing.

Further, this combi-hole includes two distinct overlapping portions in a single slot. One portion of the slot is suited to receive a standard bone screw, while the other portion of the slot is suited to receive a threaded peg oriented perpendicular to the top surface of the bone plate. Also, the combi-holes are generally oriented with the threaded portions being on the innermost end of the combination and the unthreaded portions oriented toward the ends of the bone plate. This improvement increased the flexibility of choice available to orthopedic surgeons using the device in that it was more likely that a hole would be present at a suitable anchoring point in the bone plate. Nevertheless, there are often trauma situations that are best served by the threaded portion being at the extreme ends of the bone plate and/or at various positions throughout the plate. In addition, sometimes there is no specific center of the facture—in such a situation; use of the combi-hole design is limited. The combi-hole if further limited in that it allows the fixing of a screw in either the slotted portion or the threaded portion, but not both.

While patent application no. WO01/54601 has proven advantageous because screws can be locked to the plate; the presence of an unthreaded slot limits the user's ability to have multiple orientations for the screw.

In a further development, the AO Institute has studied and proposed the use of endpegs which are rigidly fixed in the extreme ends of the bone plate. Such an arrangement has been shown to better resist the flexing of the bone than use of a bone screw alone. Flexing can otherwise loosen the connection between the bone plate and bone in other bone plate systems.

U.S. Pat. No. 5,324,290 shows a complex bone plate having slots with countersunk circular recessed cuts at intervals along the slot (a similar arrangement is shown in U.S. Pat. No. 4,696,290). It further shows the bone plate torqued against the bone so as to at least marginally, conform to the shape of the bone (see FIG. 2). Other patents of interest include U.S. Pat. Nos. 3,716,050; 3,659,595; 5,681,311; 5,261,910, and 5,364, 399, as well as German Patent application DE4341980A1, all showing combinations of conventional slots and recesses which do not fully accommodate a bone screw having a threaded head. In comparison with the combi-hole design and the friction locking design described above, what is needed is a bone plate that provides greater flexibility of choice to the surgeon. More specifically, what is needed is a bone plate that provides this choice of plate placement while reliably and permanently fixing the bone plate to the bone fragments, in any hole position.

What is needed is a bone plate that provides greater flexibility of choice to the surgeon, in a bone plate that has multiple orientations for the locking screw and thus, plate placement, while reliably and permanently fixing the bone plate to the bone fragments, in any hole position.

In addition, what is needed is a versatile bone plate having recesses which determine where the bone plate will bend, in order to avoid the threads in any holes to be bent or warped, while maintaining a smooth external surface.

Finally, what is needed is a bone plate with holes that create bi-directional compression.

SUMMARY OF THE INVENTION

The present invention relates to bone plates of complex form for use with bone screws having a head radius r. The bone plates have a main longitudinal axis, a bone-contacting bottom side and a top side with a plurality of bone screw apertures. At least one pair of the bone screw apertures forms an adjoined aperture pair. An adjoined aperture pair is defined in the figures and includes an additional relief-space contiguous to the open space of the apertures themselves. An adjoined aperture pair has a center-to-center distance d of the apertures along an axis running through the centers of the apertures. The center-to-center distance d is equal to or greater than the sum of the radii (r1+r2) of the individual bone screw heads used with the aperture pair. The adjoined pair of screw apertures is further defined by the above noted relief-space (or bar-space feature) disposed between and joining them, to provide a complex aperture the opening—which gives a portion of the complex aperture a "bar-bell" like configuration. Preferably, the additional relief-space feature is configured as either a straight slot, or as a constricted or "waisted" slot centered on, about or along the axis joining the opening of the screw apertures. When applied to a bone, two different adjoined aperture pairs are located so as to lie on opposite sides of an osteotomy site. The installation configuration of bone screws in the complex bone plate is selectable, depending on the physiology of the bone being repaired.

An object of the invention is to provide a surgeon with the option of placing two bone screws in adjacent positions so that the heads of the adjacent bone screws can abut without overlapping. Another object of the invention is to provide an orthopedic surgeon greater flexibility of choice in that a threaded peg or screw providing secure fixing can be positioned at any interval along the bone plate, including at its extreme ends or on its elbow.

DETAILED DESCRIPTION OF THE PREFERRED EMBODIMENTS

Referring now to the drawings, the details of preferred embodiments of the present invention are graphically and schematically illustrated. Like elements in the drawings are represented by like numbers, and any similar elements are represented by like numbers with a different lower case letter suffix.

Figure 1A:
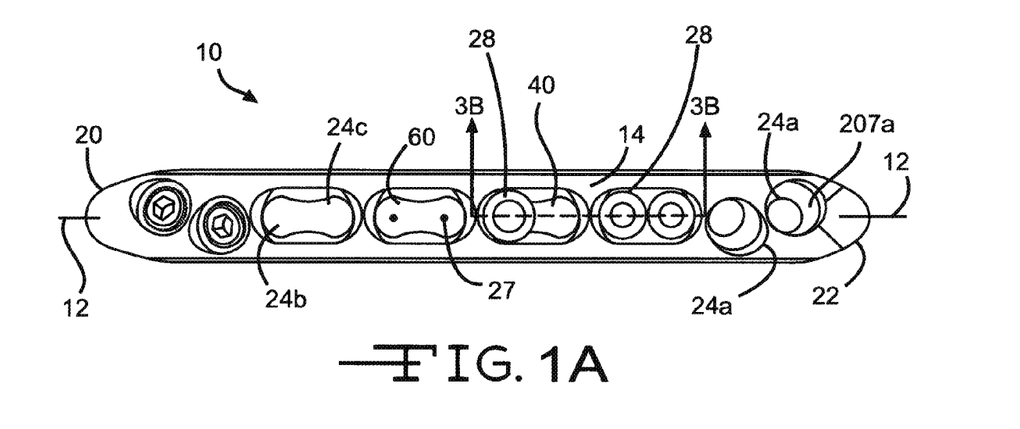
FIGS. 1A and 1B respectively are top views of a bone plate of the invention incorporating one type of relief-space, and a close-up view of the first end of the bone plate.
Figure 2A:
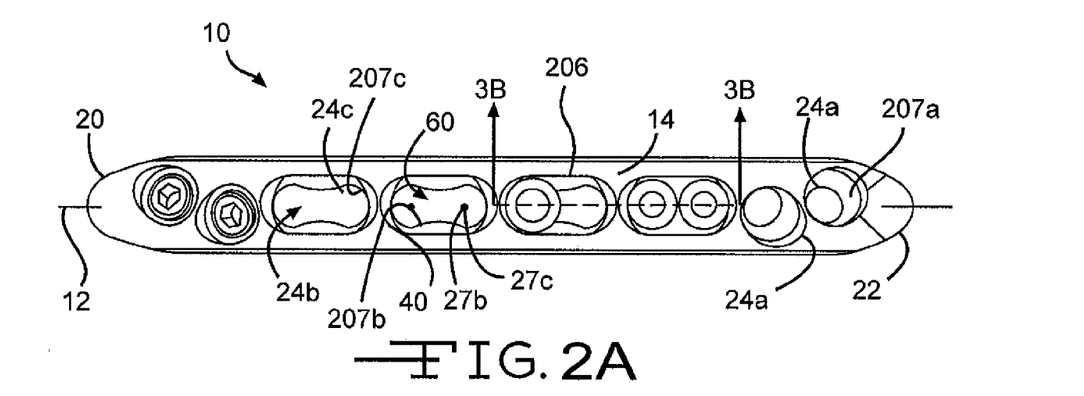
FIGS. 2A and 2B respectively are top views of a bone plate of the invention incorporating an alternative type of relief-space, and a close-up view of the first end of the bone plate.

As exemplified in FIGS. 1A and 2A, the present bone plate 10 has a main longitudinal axis 12, a bone-contacting bottom side 16 (see FIG. 4), a top side 14 and opposite first 20 and second 22 plate ends. The bone plate 10 also has a thickness 200 (see FIG. 4) that is defined between the top side 14 and the bone-contacting bottom side 16. A series of screw apertures 24 extending from the top side 14 of the plate 10 through the thickness 200 to its bottom side 16 are formed along or contacting the plate axis 12. The screw apertures 24 serve as bone screw guides through which points bone screws 28 are inserted into underlying bone to anchor the bone plate 10 to different parts or fragments 80 of a bone to be reinforced by the bone plate 10 (see FIG. 5).

Figure 3A:
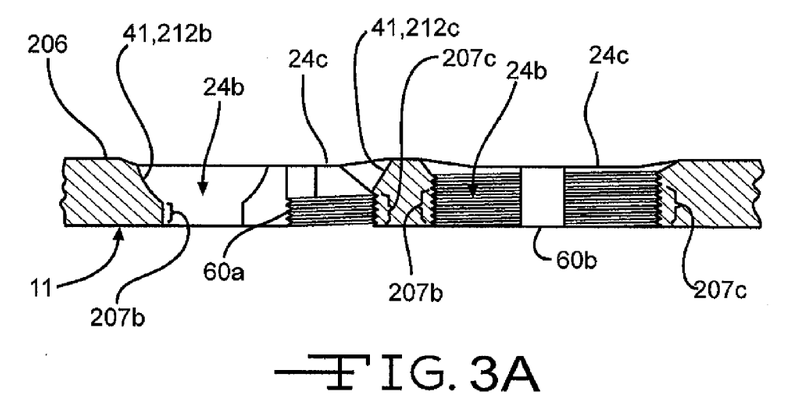
FIGS. 3A and 3B are cross-sectional side views of a section of the bone plate of FIGS. 1A and 2A taken along line 3-3, and illustrating locations for the relief-space.
Figure 3B:
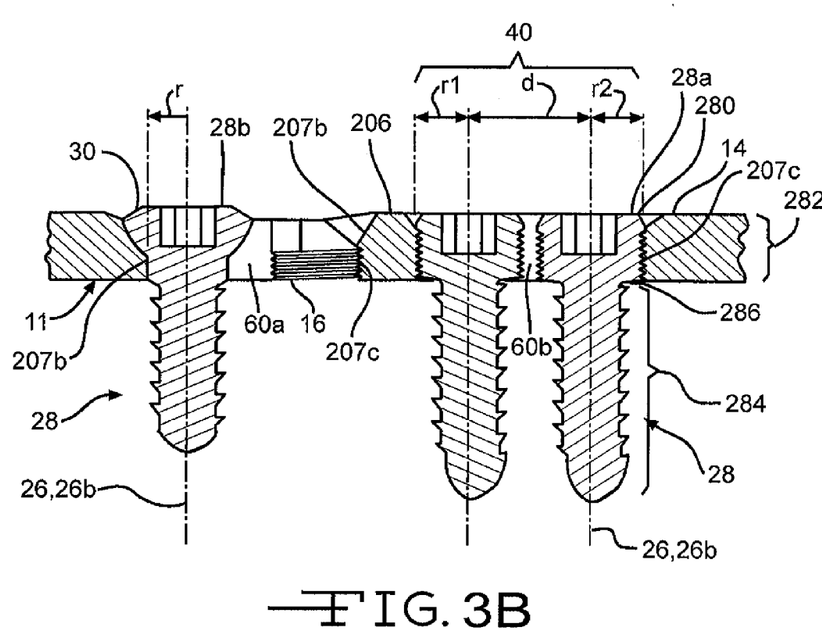
Figure 6E:
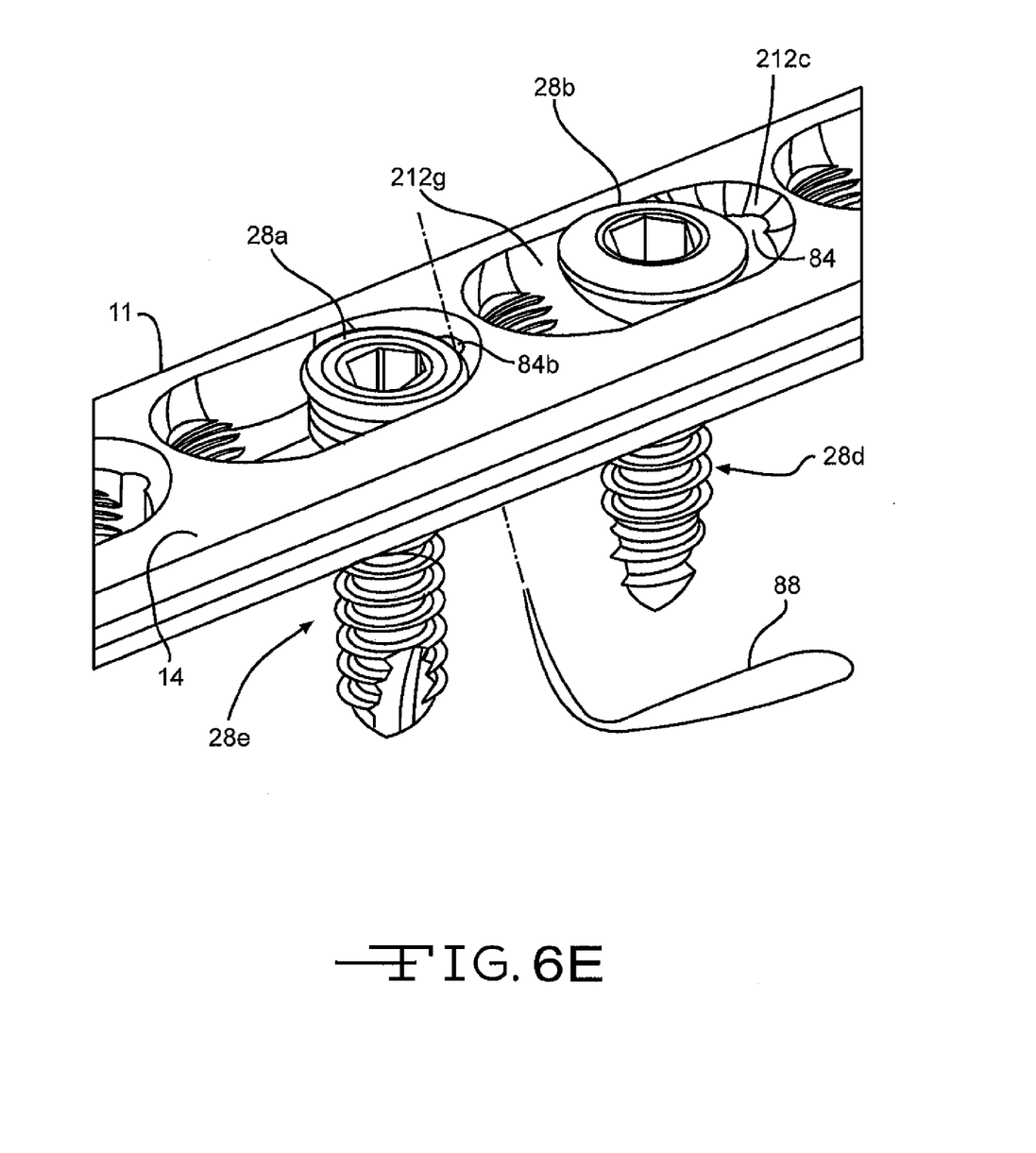
FIG. 6E is a top-side perspective view of a portion of the present bone plate with bone screws inserted into two of the complex apertures.
Figure 7:
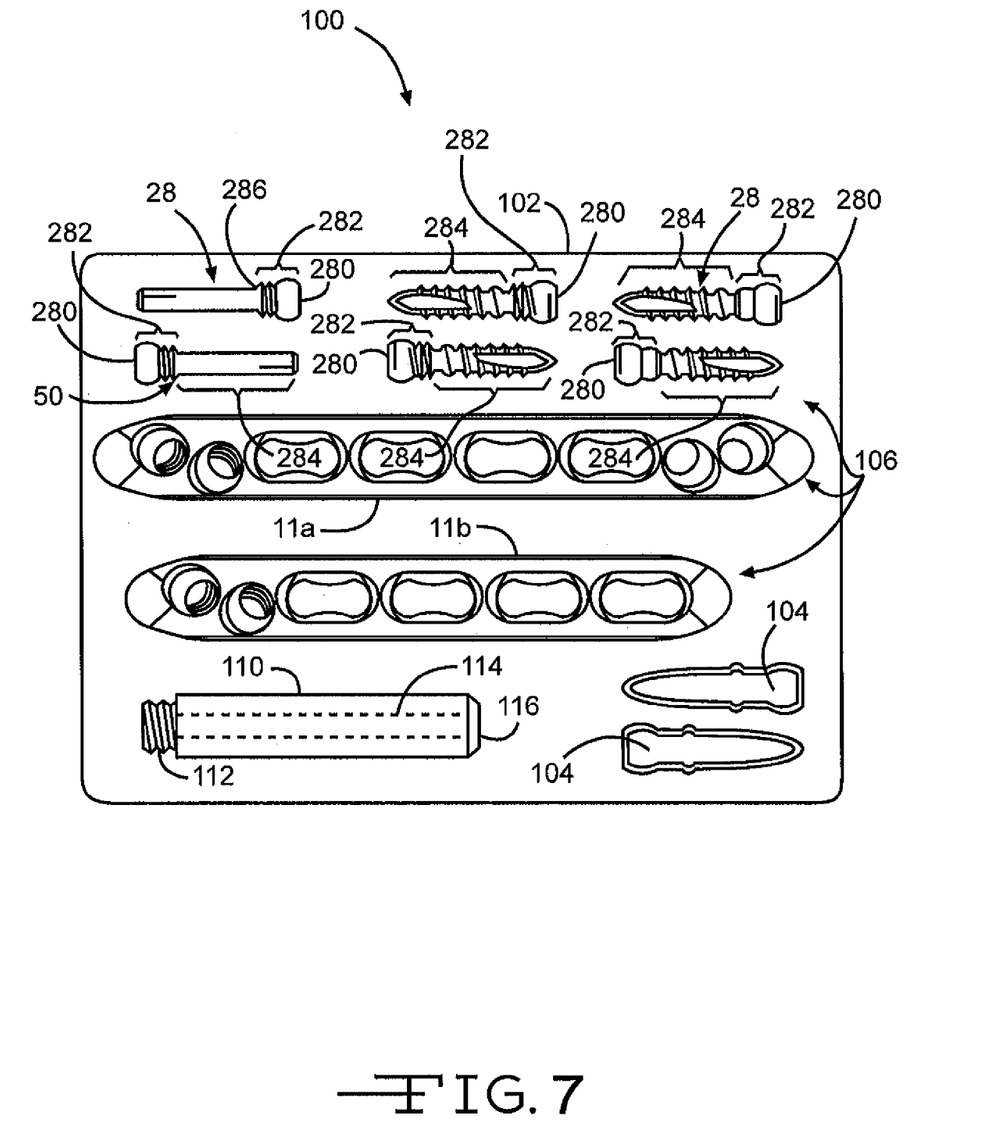
FIG. 7 is a top view of a kit of the present invention.

Bone screws 28 include a conventional locking bone screw 28a and a conventional compression bone screw 28b which are illustrated at FIGS. 3B and 7. Each bone screw has a head area 280 with a surface that allows a tool to be interconnected to the head area to apply the desired torque to the screw to allow the bone screw to enter a bone; a bone insertion area 284; and a bone plate area 282. The bone plate area 282 is positioned between the head 280 and the bone thread area's crest 286. The bone plate area 282 can be entirely threaded (element 28a in FIG. 3B), partially threaded (element 28a in FIG. 6E) or unthreaded (element 28b in FIGS. 3B, 5, and 6E).

Each screw aperture 24 has a screw axis 26 through its center 27 (the general path that a screw takes when inserted through the aperture). The screw axis 26 (see FIGS. 1B, 2B and 4) is either perpendicular 26b or angled 26a relative to the plane of the bone plate 10. The position of the screw axis depends on the need of a particular application or surgical protocol.

Complex Aperture

Additionally, the bone plate 10 of the present invention has one or more complex apertures 40. Each complex aperture comprises a pair of closely spaced apart screw apertures 24 (identified in the FIGS. as 24b and 24c) adjoined by a "relief"-space feature 60. The relief-space feature 60 is disposed between and joins the openings of the two pair of closely spaced apart screw apertures 24b and 24c). The relief space feature also provides a complex aperture having a single opening to form, at least within portions of the thickness 200 and the bone contacting bottom side 16, a "dumb-bell" or "bar-bell" like configuration. Preferably, the relief-space 60 has a portion thereof that is configured as either a straight slot 60b(see FIG. 3A) or a constricted or "waisted" slot 60a (see FIG. 3A).

Relief Space Embodiments

Figure 1B:
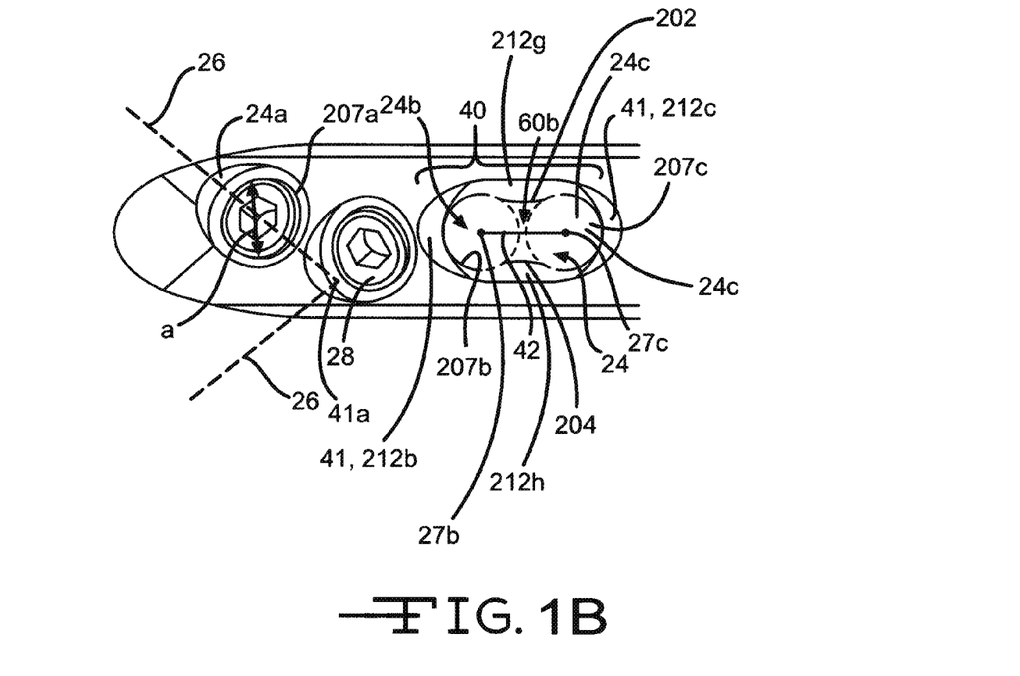
Figure 6A:
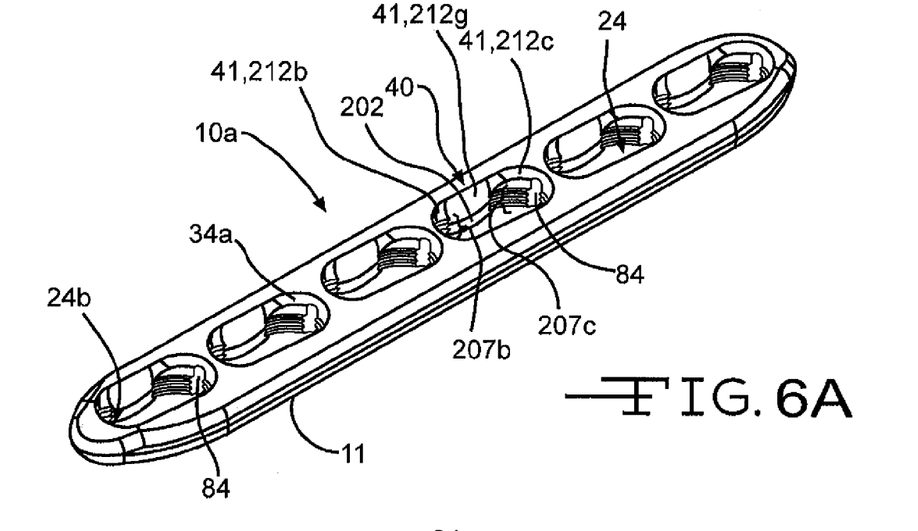
FIGS. 6A and 6B are top-side perspectives views of an alternative embodiment of the present bone plate showing (A) the full plate and (B) a detailed partial view.
Figure 6B:
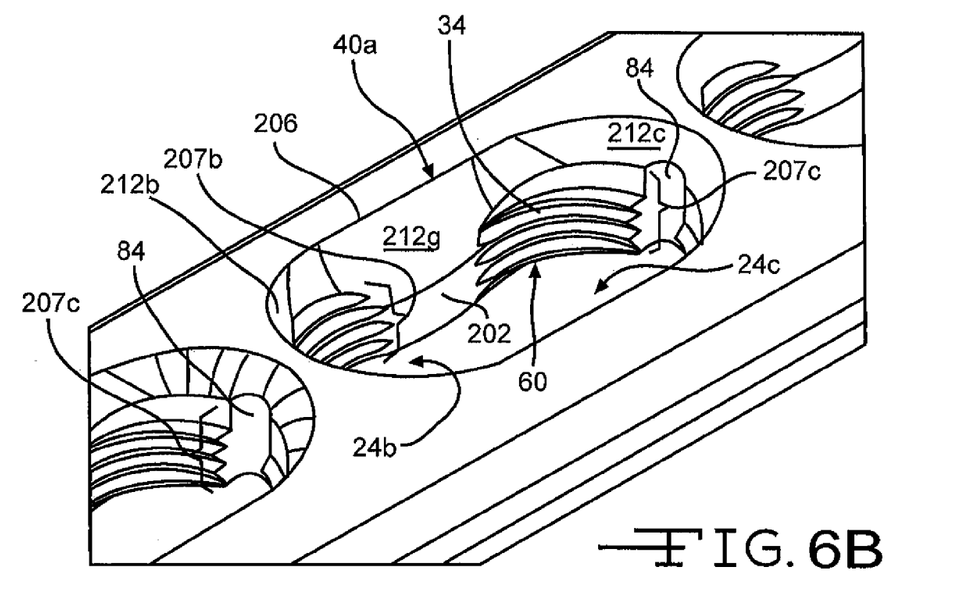
Figure 6C:
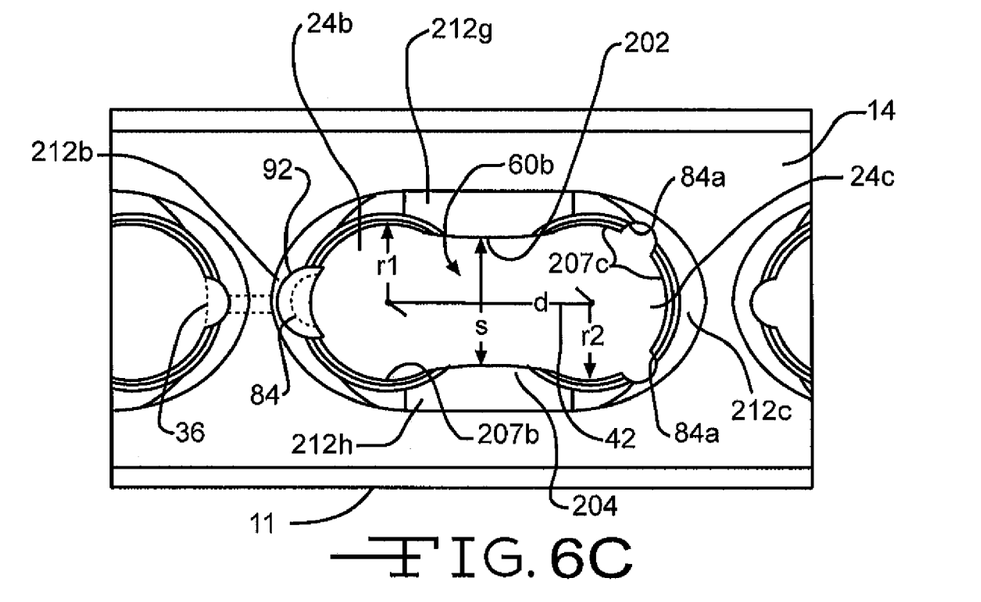
FIGS. 6C and 6D respectively are top-side and bottom-side plan views detaining respective portions of the present bone plate.
Figure 6D:
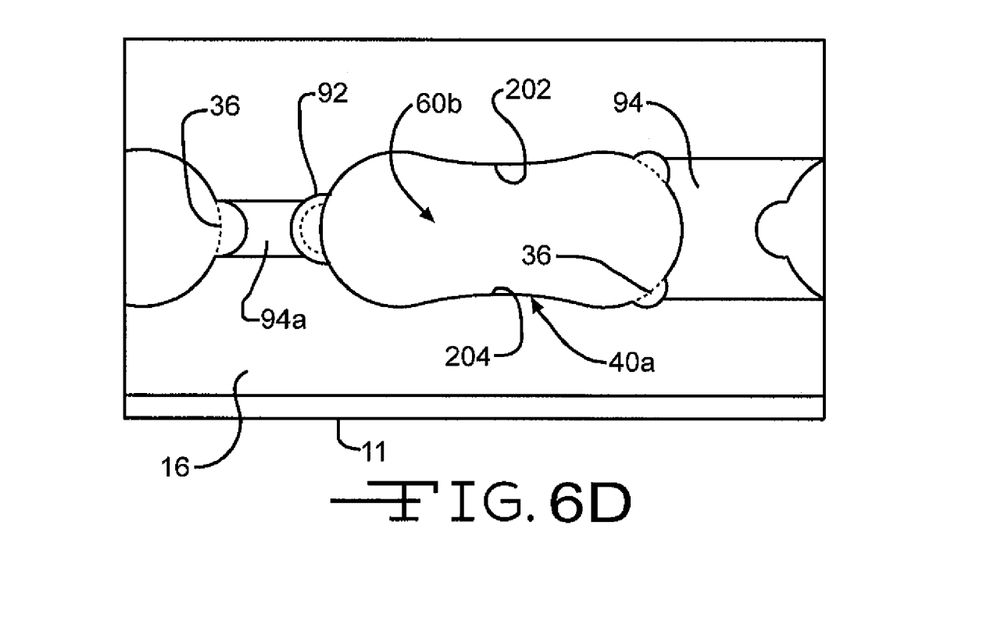

In a preferred embodiment illustrated at FIGS. 1A and 1B, the relief-space 60 has the constricted or "waisted" slot 60b. Referring to FIGS. 1B and 6C, the constricted or waisted slot 60b is defined between (a) the pair of closely spaced apart screw apertures 24b and 24c and (b) two facing arcuate walls—a first walled surface 202 and a second walled surface 204—which have their cord parallel to the radial axis 42 of the closely spaced apertures 24b and 24c.

Figure 2B:
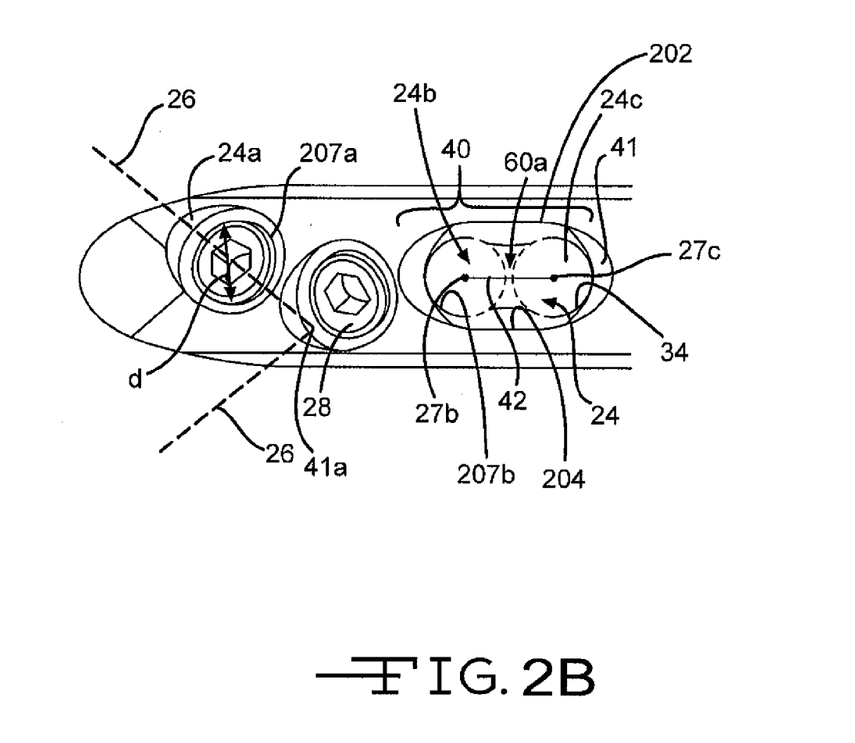

In an alternative preferred embodiment shown in FIGS. 2A and 2B, the relief space 60 has the straight-slot relief 60a. The straight-slot relief is defined between (a) the pair of closely spaced apart screw apertures 24b and 24c and (b) two facing parallel walls—the first walled surface 202 and the second walled surface 204.

Despite those differences, the straight slot 60a and the "waisted" slot 60b have some similarities. One of the similarities is that each slot of the relief-space 60 is defined by (a) the first screw aperture 24b, wherein the first screw aperture has a first radius (r1). The first radius (r1) is measured from the first screw aperture's center 27b in its seat area 207b (defined in greater detail later) to the walled surface (and if the walled surface is threaded then to the root of the threaded surface) in the first screw aperture's seat area 207b as illustrated in FIGS. 3A, 3B, 6A, and 6B. The seat area 207b can be a threaded surface, a ringed surface, or an unthreaded surface—it depends on the need of a particular application or surgical protocol that the bone plate is to be used;

(b) the second screw aperture 24c, wherein the second aperture has a second radius (r2). The second radius (r2) is measured from the second screw aperture's center 27c in its seat area 207c to the walled surface (and if the walled surface is threaded then to the root of the threaded surface) in the second screw aperture's seat area 207c as illustrated in FIGS. 3A, 3B, 6A, and 6B. The seat area 207c can also be a threaded surface, a ringed surface, or an unthreaded surface—it depends on the need of a particular application or surgical protocol that the bone plate is to be used;

(c) the first walled surface 202, and (d) the second walled surface 204.

The first walled surface 202 and the second walled surface 204 are spaced apart a distance (s) which is less than twice the distance of (i) the first radius (r1) and (ii) the second radius (r2), as illustrated at FIG. 6C, and do not contact each other in the straight slot embodiment 60a.

The relief-space is also preferably centered on a radial axis 42 (in relation to the centers 27 of the respective apertures 24b and 24c) joining the opening of the screw apertures 24b and 24c, as illustrated at FIGS. 1B, 2B, 6C.

Complex Aperture

As noted above, the bone plate 10 has at least one complex screw aperture 40 made up of two screw apertures 24b and 24c joined by a relief-space 60. Each screw aperture 24b and 24c in the complex screw aperture has a bevel surface section 41 and its respective seat area 207 b,c. Each seat area extends from the bottom of the bevel surface 41 to the bottom surface 16, as illustrated in FIGS. 3A, 3B, 6A, 6B. Whichever seat area 207 b,c embodiment is selected or used, the screw apertures 24b and 24c are joined by a relief-space 60.

Likewise, each relief space 60 is defined by the respective slot embodiment and extending from the first walled surface 202 and the second walled surface 204 toward the top surface 14 is the bevel surface 41.

However, multiplex screw apertures 40 (not shown) made up of more than two screw apertures 24 are considered a possible alternative embodiment of the current description of the complex screw aperture. In the possible alternative multiplex-complex screw aperture there is at least one pair of the of the screw apertures 24b and 24c is separated by a relief-space 60.

The complex aperture 40 has a top surface opening 206. The top surface opening 206 is positioned on the top surface 14, has a perimeter greater than the perimeter of the complex aperture's (a) first screw aperture's seat area 207b, (b) second screw aperture's seat area 207c and (c) relief slot area (defined by the first walled surface 202 and the second walled surface 204 and the seat areas 207 b,c). In addition, the top surface opening 206 initiates the bevel surface section 41.

The bevel surface section 41 is divided into at least four areas—a first compression ramp area 212b, a second compression ramp area 212c, a third compression ramp area 212g, and a fourth compression ramp area 212h. The first compression ramp area 212b extends from the top surface opening 206 downwardly and inwardly at least part way through the plate's thickness 200 to the first screw aperture's seat area 207b. Likewise, the second compression ramp area 212c extends from the top surface opening 206 downwardly and inwardly at least part way through the plate's thickness 200 to the second screw aperture's seat area 207c. The third compression ramp area 212g extends from the top surface opening 206 downwardly and inwardly at least part way through the plate's thickness 200 to the relief space's first walled surface 202. The fourth compression ramp area 212h extends from the top surface opening 206 downwardly and inwardly at least part way through the plate's thickness 200 to the relief space's second walled surface 204. In a preferred embodiment, the first walled surface 202 and second walled surface 204 are unthreaded from the respective compression ramp area 212g,h to the bottom surface 16.

The first and second compression ramp areas 212b, 212c can have the same or different ramp angles; likewise the third and fourth compression ramp areas can have the same or different ramp angles. The ramp angles are dependent on the distance from the perimeter of the top surface opening 206 to the respective seat area and relief space's respective walled surface. In view of the different ramp angles, it is evident that there is a transition compression ramp area 212f between (a) the first compression ramp area and the third compression ramp area and (b) the first compression ramp area and the fourth compression ramp area, (c) the second compression ramp area and the third compression ramp area and (d) the second compression ramp area and the fourth compression ramp area.

In a preferred embodiment, the angle of each compression ramp is designed to (1) optimize the desired force (a) from the bone screw 28 into the bone 80, (b) from the bone plate 10 onto the bone, and (2) secure the bone plate 10 against the bone's exterior surface. Each compression ramp can be a mono-faceted surface as illustrated in FIG. 6B or a multifaceted surface as illustrated in FIG. 6E.

Figure 5:
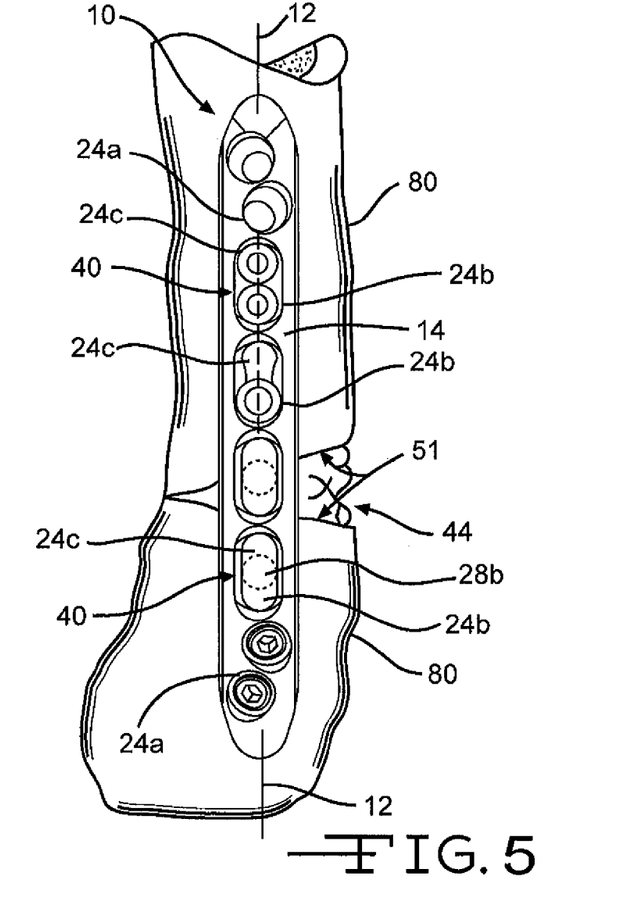
FIG. 5 is a schematic illustration of the present bone plate fixed to a bone.

Each compression ramp is also designed to align the bone screw into the proper location. For example, compression ramp 212b guides the bone screw into the seat area 207b of first aperture 24b so the bone insertion area 284 aligns with the screw aperture's 24b center 27b to obtain the desired axis 26 into the bone 80. Likewise, compression ramp 212c guides the bone screw into the seat area 207c of first aperture 24c so the bone insertion area 284 aligns with the screw aperture's 24c center 27c to obtain the desired axis 26 into the bone 80. When (a) a screw bone is inserted into (i) the first screw aperture 24b or (ii) the second screw aperture 24c or (b) a first screw bone is inserted into the first screw aperture 24b of a first complex aperture and a second screw bone is inserted into the second screw aperture 24c of the first complex aperture so the first screw bone and the second screw bone do not overlap each other and may even contact each other as illustrated in FIGS. 3B and 5, then the screw bone(s) anchors and therefore locks the bone plate 10 to the bone 80.

The compression ramps 212g and *h* also align the bone screw into the proper location. Instead of having the bone screw positioned in the respective seat area 207 of the first or second aperture 24b,c; the bone screw is positioned in the relief slot 60a or 60b. When the bone screw passes through the relief space 60 and is torqued down, the relief slot 60a,b expands and locks the screw 28b in place as illustrated at FIG. 5. In this embodiment, only one bone screw can be used in the complex aperture 40.

Additionally, the present bone plate 10 includes angled screw apertures 24a. Referring now to FIGS. 1B and 2B, two angled apertures 24a (preferably positioned proximate at least one of the plate ends 20, 22 of the bone plate 10) have screw axes 26a that are angled from the perpendicular relative to the plane of the bottom side 16 of the bone plate 10, and preferably in opposing orientations. The orientation is selectable by one of skill in the field to provide an optimal utility for a variety of operative procedures. In this particular embodiment, the angled holes 24a in the plate ends 20, 22 are inclined at an angle of approximately forty-five degrees relative to the plane of the bottom side 16 of the bone plate 10. The angled apertures 24a are disposed relative to each other to accept and to guide a bone screw 28 at opposing angles in order to securely anchor the bone plate 10 to the bone fragment 80 (see FIG. 5).

It should be noted that screw apertures 24 (24a, b, c) can be configured to be complementary to bone screws 28 having a number of configurations screw head areas 280, bone plate areas 282 and bone insertion areas 284. For example, as exemplified in FIGS. 3A and 3B a bone screw 28 can have a threaded-bone plate area 282 or an unthreaded-bone plate area 282. Additionally, a bone screw 28 with a threaded-bone plate area 282 can have a threaded-bone insertion area 284 or an unthreaded-bone insertion area 284 (see FIG. 7). Correspondingly, the screw apertures 24 can have the seat area 207b,c threaded or unthreaded as previously described to receive the desired and corresponding bone screw 28. The bone plate 10 may optionally use a locking bone peg 50, i.e., a bone screw 28 with a threaded-bone plate area 282 and unthreaded-bone insertion area 284 (see FIG. 7). Preferably, the threads cut in the head of the bone pegs 50 are designed so as to lock with the threaded apertures in a threaded seat area 207b,c in order to better ensure rigid fixing of a fracture. The locking feature used can be any of the known methods of locking threads by mechanical means.

Referring now to FIGS. 3B and 6C, the center-to-center distance d of the two screw apertures 24b,c as measured from the respective seat areas 207b,c of the complex-aperture 40 corresponds substantially to the sum of the radii of the of the two screw apertures 24b,c, i.e., r1+r2=d. This configuration enables installation of bone screws 28 through the elongated plate 11 so that the head areas 280 of the bone screws 28 can be positioned as close together as possible, and even to be touching.

Figure 4:
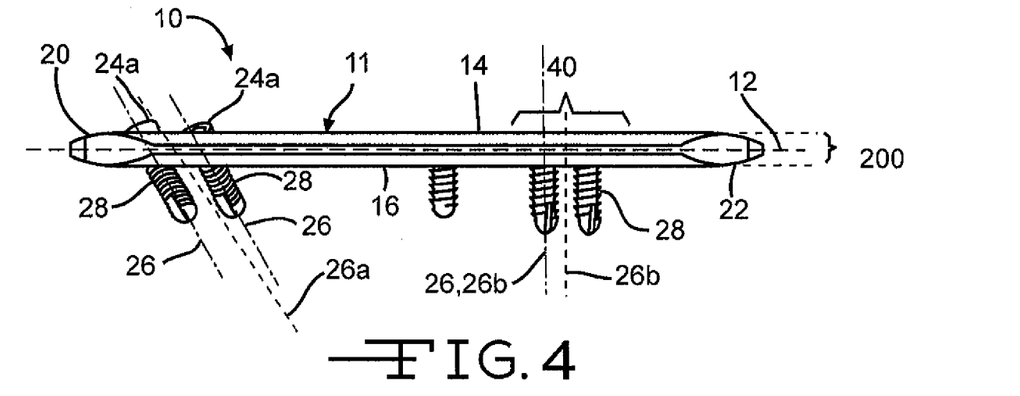
FIG. 4 is a side view of an exemplary assembly of the screws and bone plate of the present invention.

In the embodiment illustrated in FIG. 4, a pair of angled screw apertures 24a is shown at the first plate end 20 of a bone plate 10 with bone screws 28 installed through them. In this embodiment, the screw axes 26a of the angled screw apertures 24a at the first plate end 20 slant toward the second plate end 22. The general triangular configuration formed by the bone screw axes 26a, 26b with the axis 12 of the elongated plate 11 creates a triangular truss-like structure that is able to resist a wide range of forces which could otherwise tend to loosen an installed bone plate 10. Consequently, this configuration resists pull-out forces coming from a wider range of directions. Although FIG. 4 shows the screw axes 26 of the angled screw apertures 24a at the first plate end 20 slant toward the second plate end 22, they can slant in the opposite direction as shown in FIGS. 1B and 2B. Additionally, the screw apertures 24 proximate the plate ends 20, 22 are independent of screw apertures 24 located in the mid-section of the bone plate 10. It should be noted that in other preferred embodiments, a pair of angled screw apertures 24a can be disposed at both first and second plate ends 20, 22 of a bone plate 10 (see FIGS. 1A & 2A), or at any other location on the elongated plate 11.

Referring now to FIG. 5, in another embodiment, the bone plate 10 is particularly suited for femoral osteotomies 44, correcting medial patellar luxations, and/or other corrective osteotomies of the femur. The bone plate 10 has a main longitudinal axis 12, a bone contacting bottom side 16 and a top side 14 with one or more complex apertures 40 having a pair of closely adjacent screw apertures 24b,c, which communicate through the plate 11 from the top side 14 to the bottom side 16. The closely adjacent pairs of screw apertures 24 b,c have a multifaceted screw head areas 280 and bone plate areas 282. Preferably, when the elongated plate 11 is applied to a bone 80, two complex apertures 40 are disposed to lie on opposite sides 51 of an osteotomy site 44. In the figure shown, the bone plate 10 also has two pairs of angled apertures 24a—one pair on or near the first plate end 20 and the other pair on or near the second plate end 22. The pairs of screw apertures 24 can act together as compression fittings. When applied to a bone part 80, each pair of screw apertures 24b,c can be disposed to lie on opposite sides 51 of an osteotomy site 44.

An alternative embodiment of the present bone plate 10 is illustrated in FIGS. 6A to 6E. In this embodiment the complex apertures 40 are similar to the complex apertures described above, but differ in that they have a relief notch 84 disposed in the screw head seat 207b,c 34 portion of one or both screw apertures 24b,c. The relief notch 84 provides desirable advantages that are not similarly accomplished in their absence. For example, as shown in FIG. 6C, a self-locking insert 92 can be disposed in the notch 84 to provide increased friction for setting a threaded bone plate area 282 set in a threaded seat area 207b,c. As also illustrated in FIG. 6C, it is intended that a screw aperture 24 may have more than one relief notch 84a. A further example of an advantage of the present notch feature is illustrated in FIG. 6E, which illustrates that a tensioning wire 88 may be looped around a first bone screw 28d, passed along the bottom side 16 of the elongated plate 11 and the ends of the wire drawn up to the top side 14 of the elongated plate 11 through the recess notch 84b in an adjacent second bone screw 28e. In the embodiment illustrated in FIG. 6D, the bottom-side 16 of the elongated plate 11 is provided with a clearance channel 94, 94a recessed into the surface of the bottom-side of the plate 11. The clearance channel communicates with the relief notch 84 to provide a path for the tensioning wire 88 to be easily removed through the relief notch 84 after the bone screws 28 have been set against the bone plate 10.

The notch feature 84 can be a part of the screw aperture 24a,b,c having threaded seat 207a,b,c with the bevel area 41 between the threaded seat area and the top surface 14. The notch feature 84 is not, however, a part of the measurement for the first radius (r1) or the second radius (r2) as confirmed in FIG. 6C.

Referring now to FIG. 7, in another embodiment, includes an orthopedic bone plate kit 100 which includes a compartmented container 102, preferably having shaped compartment spaces 104 corresponding to the shape of the kit item 106 to be received in the shaped compartment space 104. Kit items 106 contained in the kit 100 include one or more bone plates 10 having the same or similar elongated plate features 11a & 11b, and a plurality of bone screws 28. Note that the bone screws 28 may be of a variety of somewhat different configurations practicable with the screw apertures 24 of the present invention. As examples, included in the kit 100 shown are: threaded-head bone screws, unthreaded-head bone screws (both with threaded shanks) and threaded-head pegs—(i.e., an unthreaded shank), all can be of various lengths. Additionally shown in the kit 100 is a drill guide 110. The drill guide 110 has a threaded end 112 that can screw into the threaded-seat 207b and c on a screw aperture 24. The drill guide has a hollow bore 114 that serves as a guide for a drill bit (not shown) for use to drill a pilot hole in the bone for the bone screw 28 that is to be inserted into the bone through the screw aperture 24.

In an advantage, unlike the case with overlapping threaded screw apertures (i.e., their center-to-center distance being less than d), a surgeon is able to place two bone screws 28 side by side, in a very close proximate position wherein the bone screws' heads can abut one another.

In another advantage, the invention enables the spacing between bone screws that is so close that the surgeon is able to maintain a standard spacing such as that purveyed by the AO Institute, founded by Synthes S. A.

In another advantage, where a fracture runs between screw apertures 24, a surgeon is able to place two bone screws 28 on opposite sides of the fracture, thereby better fixing the broken bone parts 80 together for optimal healing.

In an advantage of the invention, the bone plate 10 provides greater flexibility of choice to the surgeon in that a threaded-head peg 50 providing secure fixing can be positioned at any interval along the elongated plate 11, including at its extreme ends.

In another advantage, the bone plate 10 provides greater flexibility of choice by providing multiple complex apertures 40 oriented either along the longitudinal axis 12 of the elongated plate 11, oriented at an angle to the longitudinal axis 12, and staggered along the axis 12.

In still another advantage, the threaded head apertures 34a of the elongated plate 11 are provided with threads cut for a screw axis 26 perpendicular to the top side 14 of the elongated plate 11, as well as for a screw axis 26 at a non-perpendicular angle to the top side 14 of the elongated plate 11.

The configuration of this complex bone plate 10 may vary, depending on the physiology of the patient. An illustration of the flexibility of application of the plate 80 is its flexible use in osteotomy.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A bone plate adapted for use in situ to fix a spatial relationship of at least two bone parts, the bone plate comprising:
   a) an elongated plate having a longitudinal axis, a bone contacting bottom side, a top side, a thickness between the bottom and top sides with at least one complex screw aperture extending through the plate thickness and comprised of a first screw aperture and a second screw aperture adjoined by a relief zone disposed between the first and second apertures;
   b) wherein the first screw aperture of the complex aperture has a first radius ($r_1$) measured from a first center of a first seat thereof and the second screw aperture has a second radius ($r_2$) measured from a second center of a second seat thereof, and
   c) wherein each of the first and second apertures of the complex aperture comprises a beveled upper surface extending from the top side of the plate downwardly and inwardly part way through the plate thickness to a lower, threaded seat portion extending from where the beveled surface ends to the bottom side of the bone plate, and
   d) wherein the relief zone adjoining the first and second apertures is defined by two opposed unthreaded surfaces, each of them forming an upper unthreaded compression ramp extending from the top side downwardly and inwardly at least part way through the plate thickness to an unthreaded lower portion, and
   e) wherein the complex aperture has a center-to-center distance (d) measured along the parallel radii $r_1$ and $r_2$ and the relief zone disposed between the adjoined first and second screw apertures that is at least equal to a sum of the radii $r_1$ and $r_2$, and
   f) wherein the two opposed unthreaded surfaces of the relief zone are spaced apart by a distance (s) that is less than twice the distance of $r_1$ and less than twice the distance of $r_2$.

2. The bone plate of claim 1, wherein at least one of the radii $r_1$ and $r_2$ of the respective first and second screw apertures extend into the relief-zone.

3. The bone plate of claim 1, wherein at least one of the first and second screw apertures has a head-seat that is selected from the group consisting of:
   a) a threaded head seat,
   b) a ringed surface seat,
   c) a ridged surface seat, and
   d) a tapered lead-in surface seat in combination with a threaded head seat, a ringed surface seat, and a ridged surface seat.

4. The bone plate of claim 1, wherein the relief-zone has a relief slot configured as a waisted relief or a straight relief slot.

5. The bone plate of claim 1, wherein the beveled upper surface of at least one of the first and second screw apertures is a threaded surface portion.

6. The bone plate of claim 1, wherein the first screw aperture or the second screw aperture of the complex aperture has at least one relief notch set into its beveled upper surface.

7. The bone plate of claim 1, wherein the first screw aperture or the second first screw aperture of the complex aperture has at least one relief notch set into its beveled upper surface and a self-locking material plug retained in the relief notch.

8. A method of installing a bone plate in situ to fix a spatial relationship of at least two bone parts of a bone, the method comprising the steps of:
   a) providing the bone plate of claim 1;
   b) positioning the bone plate over the bone with the relief zone positioned over the bone surface feature to which the bone plate is to be fixed; and
   c) installing a single threaded head bone screw in either the first or the second threaded screw apertures of a first complex aperture to anchor the bone plate to the bone part;
   d) followed by:
      i) installing a first threaded head bone screw in the first screw aperture of a second complex aperture and a second threaded head bone screw in the second screw aperture of the second complex aperture of the bone plate so that the first bone screw and the second bone screw have their respective threaded heads relatively close to each other to thereby anchor the bone plate to the bone part; or
      ii) installing an unthreaded head bone screw in the relief zone to compress the bone plate to the bone part to thereby anchor and/or compress the bone plate to one of the bone parts and then installing at least one additional bone screw in another of the bone parts to fix the spatial relationship between the two bone parts.

9. An orthopedic kit comprising:
   a) a compartmented container having compartment spaces for receiving items to be contained in the kit;
   b) a first item of the kit being at least one bone plate of claim 1; and
   c) a second item of the kit being a plurality of bone screws with threaded heads and unthreaded heads.

10. The kit of claim 9 further comprising a drill guide having a hollow bore extending to opposite guide ends, wherein a first one of the guide ends is configured to securely engage the complex screw aperture of the bone plate as a guide for a drill bit used to drill a pilot hole in a bone for a bone screw that is to be inserted into the bone through one of the first and second screw apertures of the complex aperture.

11. A bone plate adapted for use in situ to fix a spatial relationship of two bone parts, the bone plate comprising:
   a) an elongated plate having a longitudinal axis, a bone contacting bottom side with a recessed clearance channel disposed along the axis, a top side, a thickness between the bottom and top sides with at least one complex aperture extending through the plate thickness and comprised of a first screw aperture and a second screw aperture adjoined by a relief zone disposed between the first and second apertures;
   b) wherein the first screw aperture of the complex aperture has a first radius ($r_1$) measured from a first center of a first seat thereof and the second screw aperture has a second radius ($r_2$) measured from a second center of a second seat thereof, and
   c) wherein each of the first and second apertures of the complex aperture comprises a beveled upper surface extending from the top side of the plate downwardly and inwardly part way through the plate thickness to a lower, threaded seat portion extending from where the beveled surface ends to the bottom side of the bone plate, and;
   d) wherein the relief-zone adjoining the first and second apertures is defined by two opposed unthreaded surfaces, each of them forming an upper unthreaded compression ramp extending from the top side downwardly and inwardly at least part way through the plate thickness to an unthreaded lower portion, and
   e) wherein the complex aperture has a center-to-center distance (d) measured along the parallel radii $r_1$ and $r_2$ and the relief zone disposed between the adjoined first and second screw apertures is at least equal to a sum of the radii $r_1$ and $r_2$, and
   f) wherein the two opposed unthreaded surfaces of the relief zone are spaced apart by a distance (s) that is less than twice the distance of $r_1$ and less than twice the distance of $r_2$; and
   g) at least one of the complex apertures has the relief zone disposed between a first threaded screw aperture and a second screw aperture.

12. The bone plate of claim 11, wherein the first screw aperture or the second screw aperture of the complex aperture has at least one relief notch set into its beveled upper surface.

13. The bone plate of claim 1 wherein a first bone screw is positionable in the first screw aperture and a second bone screw is positionable in the second screw aperture such that the first bone screw contacts the second bone screw.

14. The bone plate of claim 1, wherein a first bone screw is positionable in the first screw aperture and a second bone screw is positionable in the second screw aperture such that the first bone screw contacts the second bone screw.

15. The bone plate of claim 1 wherein the complex aperture is adapted to receive:
   a) a single threaded head bone screw in the first or second screw apertures of the complex aperture to anchor the elongated plate to a bone part;
   b) two threaded head bone screws, the first of them being positionable in the first screw aperture of the complex aperture and the second threaded head bone screw being positionable in the second screw aperture of the complex aperture so the first threaded head bone screw and the second threaded head bone screw have their respective threaded heads close to each other when properly positioned to anchor the elongated plate to the bone part; or
   c) an unthreaded head bone screw is positionable at the relief zone to compress the elongated plate to the bone part.

16. A bone plate having a thickness extending from a bone-contacting bottom side to a top side with at least two complex apertures extending through the plate thickness, each complex aperture comprised of a first screw aperture and a second screw aperture adjoined by a relief-space,
   a) wherein the first screw aperture of one of the at least two complex apertures has a first radius ($r_1$) measured from a first center of a first seat thereof and the second screw aperture of the one of the at least two complex apertures has a second radius ($r_2$) measured from a second center of a second seat thereof, and
   b) wherein each of the first and second apertures of the one of the at least two complex apertures comprises a beveled upper surface extending from the top side of the plate downwardly and inwardly part way through the plate thickness to a lower, threaded seat portion extending from where the beveled surface ends to the bottom side of the bone plate, and
   (c) wherein the relief zone adjoining the first and second apertures of the one of the at least two complex apertures is defined by two opposed unthreaded surfaces, each of them forming an unthreaded compression ramp extending from the top side downwardly and inwardly at least part way through the plate thickness to an unthreaded lower portion, and d) wherein the one of the at least two complex apertures has a center-to-center distance (d) measured along the parallel radii $r_1$ and $r_2$ and the relief zone disposed between the adjoined first and second screw apertures that is at least equal to a sum of the radii $r_1$ and $r_2$, and e) wherein the two opposed unthreaded surfaces of the relief zone are spaced apart by a distance (s) that is less than twice the distance of $r_1$ and less than twice the distance of $r_2$, f) wherein the lower, threaded seat portion of the first aperture, the unthreaded lower portion of the relief zone and the lower, threaded seat portion of the second aperture provide a bar-bell shape extending from where the beveled upper surfaces of the respective first and second apertures and the upper unthreaded compression ramp of the relief zone end at the bar-bell shape to the bottom side of the bone plate, g) the first threaded lower portion of the first aperture and the second threaded lower portion of the second aperture each being adapted to lock with threads of a corresponding bone screw; and h) the unthreaded lower portion of the relief zone being adapted to receive a corresponding bone screw.

17. A bone plate having a thickness extending from a bone-contacting bottom side to a top side with at least one complex aperture extending through the plate thickness, the complex aperture comprised of a first screw aperture and a second screw aperture adjoined by a relief-space, a) wherein the first screw aperture of the complex aperture has a first radius ($r_1$) measured from a first center of a first seat thereof and the second screw aperture of the complex aperture has a second radius ($r_2$) measured from a second center of a second seat thereof, and b) wherein each of the first and second apertures of the complex aperture comprises a beveled upper surface extending from the top side of the plate downwardly and inwardly part way through the plate thickness to a lower, threaded seat portion extending from where the beveled surface ends to the bottom side of the bone plate, and c) wherein the relief zone adjoining the first and second apertures of the complex aperture is defined by two opposed unthreaded surfaces, each of them forming an unthreaded compression ramp extending from the top side downwardly and inwardly at least part way through the plate thickness to an unthreaded lower portion, and d) wherein the complex aperture has a center-to-center distance (d) measured along the parallel radii $r_1$ and $r_2$ and the relief zone disposed between the adjoined first and second screw apertures that is at least equal to a sum of the radii $r_1$ and $r_2$, and e) wherein the two opposed unthreaded surfaces of the relief zone are spaced apart by a distance (s) that is less than twice the distance of $r_1$ and less than twice the distance of $r_2$, f) wherein the first screw aperture and the second screw aperture have an offset of a given distance between their respective first and second centers thereof, and the first and second centers are staggered about a longitudinal axis of the bone plate;

g) wherein the lower, threaded seat portion of the first aperture, the unthreaded lower portion of the relief zone and the lower, threaded seat portion of the second aperture provide a bar-bell shape extending from where the beveled upper surfaces of the respective first and second apertures and the upper unthreaded compression ramp of the relief zone end at the bar-bell shape to the bottom side of the bone plate, h) the first threaded lower portion of the first aperture and the second threaded lower portion of the second aperture each being adapted to lock with threads of a corresponding bone screw; and i) the unthreaded lower portion of the relief zone being adapted to receive a corresponding bone screw.

18. A bone plate having a thickness extending from a bone-contacting bottom side to a top side with at least one complex aperture extending through the plate thickness, the complex aperture comprised of a first screw aperture, a second screw aperture adjoined by a relief-space, a) wherein the first screw aperture of the at least one complex aperture has a first radius ($r_1$) measured from a first center of a first seat thereof and the second screw aperture of the at least one complex aperture has a second radius ($r_2$) measured from a second center of a second seat thereof, and b) wherein each of the first and second apertures of the at least one complex aperture comprises a beveled upper surface extending from the top side of the plate downwardly and inwardly part way through the plate thickness to a lower, threaded seat portion extending from where the beveled surface ends to the bottom side of the bone plate, and c) wherein the relief zone adjoining the first and second apertures of the at least one complex aperture is defined by two opposed unthreaded surfaces, each of them forming an unthreaded compression ramp extending from the top side downwardly and inwardly at least part way through the plate thickness to an unthreaded lower portion, and d) wherein the at least one complex aperture has a center-to-center distance (d) measured along the parallel radii $r_1$ and $r_2$ and the relief zone disposed between the adjoined first and second screw apertures that is at least equal to a sum of the radii $r_1$ and $r_2$, and e) wherein the two opposed unthreaded surfaces of the relief zone are spaced apart by a distance (s) that is less than twice the distance of $r_1$ and less than twice the distance of $r_2$, f) wherein the lower, threaded seat portion of the first aperture, the unthreaded lower portion of the relief zone and the lower, threaded seat portion of the second aperture provide a bar-bell shape extending from where the beveled upper surfaces of the respective first and second apertures and the upper unthreaded compression ramp of the relief zone end at the bar-bell shape to the bottom side of the bone plate, g) the first threaded lower portion of the first aperture and the second threaded lower portion of the second aperture each being adapted to lock with threads of a corresponding bone screw; and h) the unthreaded lower portion of the relief zone being adapted to receive a corresponding bone screw.

19. A bone plate having a thickness extending from a bone-contacting bottom side to a top side with at least one complex aperture extending through the plate thickness, wherein the complex aperture is comprised of a compression ramp having an oval shape at the top side of the plate with the compression ramp extending from the top side downwardly and inwardly part way through the plate thickness to a lower portion having a bar-bell shape, the bar-bell shape provided by a first screw aperture and a second screw aperture adjoined by a relief zone disposed between the first and second apertures,
   a) wherein the first screw aperture has a first radius ($r_1$) measured from a first center thereof and the second screw aperture has a second radius ($r_2$) measured from a second center thereof, and
   b) wherein the first and second apertures comprise a lower, threaded seat portion extending from where the compression ramp ends to the bottom side of the bone plate, and
   c) wherein the relief zone adjoining the first and second apertures has an unthreaded lower portion, and
   d) wherein the complex aperture has a center-to-center distance (d) measured along the parallel radii $r_1$ and $r_2$ and the relief zone disposed between the adjoined first and second screw apertures that is at least equal to a sum of the radii $r_1$ and $r_2$, and
   e) wherein the two opposed unthreaded surfaces of the relief zone are spaced apart by a distance (s) that is less than twice the distance of $r_1$ and less than twice the distance of $r_2$.

20. A bone plate having a thickness extending from a bone-contacting bottom side to a top side with at least one complex aperture extending through the plate thickness, wherein the complex aperture is comprised of a compression ramp having an oval shape at the top side of the plate with the compression ramp extending from the top side downwardly and inwardly part way through the plate thickness to a lower portion having a bar-bell shape, the bar-bell shape provided by a first screw aperture and a second screw aperture adjoined by a relief zone disposed between the first and second apertures,
   a) wherein the first screw aperture has a first radius ($r_1$) measured from a first center thereof and the second screw aperture has a second radius ($r_2$) measured from a second center thereof, and
   b) wherein the first and second apertures comprise a lower, threaded seat portion extending from where the compression ramp ends to the bottom side of the bone plate, and
   c) wherein the relief zone adjoining the first and second apertures has an unthreaded lower portion, and
   d) wherein the complex aperture has a center-to-center distance (d) measured along the parallel radii $r_1$ and $r_2$ and the relief zone disposed between the adjoined first and second screw apertures that is greater than a sum of the radii $r_1$ and $r_2$, and
   e) wherein the two opposed unthreaded surfaces of the relief zone are spaced apart by a distance (s) that is less than twice the distance of $r_1$ and less than twice the distance of $r_2$.

21. The bone plate of claim 1 wherein the respective beveled surfaces of the first and second apertures extend downwardly and inwardly from the upper surface to the lower threaded surface at either the same of different angles.

22. A bone plate, comprising:
   a) an elongated plate having a longitudinal axis, a bone contacting bottom side, a top side, a thickness between the bottom and top sides with at least one complex screw aperture extending through the plate thickness and comprised of a first screw aperture and a second screw aperture adjoined by a relief zone disposed between the first and second apertures;
   b) wherein the first screw aperture of the complex aperture has a first radius ($r_1$) measured from a first center of a first seat thereof and the second screw aperture has a second radius ($r_2$) measured from a second center of a second seat thereof, and
   c) wherein each of the first and second apertures of the complex aperture comprises a beveled upper surface extending from the top side of the plate downwardly and inwardly part way through the plate thickness to a partially cylindrical wall surface that, in turn, extends downwardly to a lower, threaded seat portion extending from where the partially cylindrical wall surface ends to the bottom side of the bone plate, and
   d) wherein the relief zone adjoining the first and second apertures is defined by two opposed unthreaded surfaces, each of them forming an upper unthreaded compression ramp extending from the top side downwardly and inwardly at least part way through the plate thickness to an unthreaded lower portion, and
   e) wherein the complex aperture has a center-to-center distance (d) measured along the parallel radii $r_1$ and $r_2$ and the relief zone disposed between the adjoined first and second screw apertures that is at least equal to a sum of the radii $r_1$ and $r_2$, and
   f) wherein the two opposed unthreaded surfaces of the relief zone are spaced apart by a distance (s) that is less than twice the distance of $r_1$ and less than twice the distance of $r_2$.

23. The bone plate of claim 22 wherein the respective beveled surfaces of the first and second apertures extend downwardly and inwardly from the upper surface to the partially cylindrical wall surface at either the same of different angles.

* * * * *